United States Patent
Cramer et al.

(10) Patent No.: US 7,037,415 B2
(45) Date of Patent: May 2, 2006

(54) SENSOR ELEMENT OF A GAS SENSOR

(75) Inventors: Berndt Cramer, Leonberg (DE);
Carsten Springhorn, Stuttgart (DE);
Detlef Heimann, Gerlingen (DE);
Gudrun Oehler, Stuttgart (DE);
Margret Schuele, Weil der Stadt (DE);
Bernd Schumann, Rutesheim (DE);
Thorsten Ochs, Schwieberdingen (DE);
Sabine Thiemann-Handler, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 10/432,815

(22) PCT Filed: Nov. 20, 2001

(86) PCT No.: PCT/DE01/04353

§ 371 (c)(1),
(2), (4) Date: Dec. 16, 2003

(87) PCT Pub. No.: WO02/42760

PCT Pub. Date: May 30, 2002

(65) Prior Publication Data

US 2004/0089054 A1    May 13, 2004

(30) Foreign Application Priority Data

Nov. 23, 2000    (DE)    .................... 100 58 014

(51) Int. Cl.
*G01N 27/26*    (2006.01)

(52) U.S. Cl. .................... 204/429
(58) Field of Classification Search .............. 204/429, 204/428, 427, 426
See application file for complete search history.

(56) References Cited

U.S. PATENT DOCUMENTS

| | | | | |
|---|---|---|---|---|
| 3,685,875 A | * | 8/1972 | Dee ........................... | 384/121 |
| 4,164,462 A | * | 8/1979 | Ichikawa et al. ........... | 204/429 |
| 4,863,583 A | * | 9/1989 | Kurachi et al. ............. | 204/424 |
| 5,368,713 A | * | 11/1994 | Friese et al. ................ | 204/429 |
| 5,423,973 A | * | 6/1995 | Friese et al. ................ | 204/426 |
| 5,593,558 A | * | 1/1997 | Sugino et al. .............. | 204/429 |
| 5,893,968 A | | 4/1999 | Kato | |
| 6,409,899 B1 | * | 6/2002 | Satou et al. ................ | 204/429 |

FOREIGN PATENT DOCUMENTS

| | | |
|---|---|---|
| EP | 0 678 740 | 10/1995 |
| EP | 0 798 555 | 10/1997 |
| EP | 1 006 354 | 6/2000 |

\* cited by examiner

*Primary Examiner*—Michael Cygan
(74) *Attorney, Agent, or Firm*—Kenyon & Kenyon LLP

(57) ABSTRACT

A sensor element of a gas sensor is described, this sensor being used to determine the concentration of at least one component of a gas mixture, in particular in exhaust gases of internal combustion engines. It includes at least two electrodes which are situated in an internal gas space which is in direct contact with the gas mixture, the one electrode containing a first material and the second electrode containing a second material. The internal gas space contains a means which acts physically and/or chemically to prevent diffusion of metal between the electrodes.

12 Claims, 2 Drawing Sheets

SENSOR ELEMENT OF A GAS SENSOR

FIELD OF THE INVENTION

The present invention relates to a sensor element of a gas sensor for determining the concentration of a component of a gas mixture.

BACKGROUND INFORMATION

Electrodes of a wide variety of compositions, depending on the application, are provided in gas sensors based on solid electrolytes. Catalytically active electrodes are made of platinum or platinum/rhodium alloys, for example, whereas catalytically inactive electrodes are made of gold or gold alloys. These electrodes are located in internal gas spaces of the sensor, for example, and electrodes of different compositions may be provided in one and the same gas space, depending on the sensor design. Production of such sensors includes at least one high-temperature sintering operation, which may result in contamination of the electrodes with metal constituents of the other electrode. This results in inactivation of catalytically active electrodes due to gold inclusions, for example, or conversely an increased catalytic activity of gold electrodes due to contamination with rhodium or possibly platinum. Both effects negatively impact the sensitive properties of the sensor.

European Published Patent Application No. 678 740 describes a sensor for determining the $NO_x$ content of gas mixtures in which electrodes used to monitor the oxygen content within the sensor are made of a gold/platinum alloy, and electrodes for decomposing nitrogen oxides are made of rhodium. Both types of electrodes may be optionally physically separated from one another by a diffusion barrier.

An object of the present invention is to make available a gas sensor for determining the concentration of a component of a gas mixture in which mutual contamination of electrodes is prevented without significantly interfering with access of the gas to be analyzed to the electrodes.

SUMMARY OF THE INVENTION

The sensor element according to the present invention has the advantage that the sensor element has a means for preventing diffusion of metal between the electrodes of the sensor element and thus preventing mutual contamination of electrodes having different compositions at elevated temperatures. This makes it possible to provide a sensor having a high sensitivity to the gas which is to be determined. Access of the gas to be analyzed to the electrodes is not significantly impaired.

Advantageous refinements of and improvements on the sensor element characterized in the main claim are possible through the measures characterized in the subclaims. For example, use of a diffusion barrier applied to the surface of at least one electrode permits an effective means of preventing contamination of electrodes.

Another advantageous embodiment has a lengthened diffusion path between electrodes of different types, the respective electrodes preferably being situated at different levels of layers of the sensor.

It is particularly advantageous to use a layer of a material that absorbs metal vapor as the means to prevent the dissemination of metal vapors, because not only does this prevent the metal vapors from reaching the electrodes but also it actually removes the vapors from the gas space.

DETAILED DESCRIPTION

Figure 1:
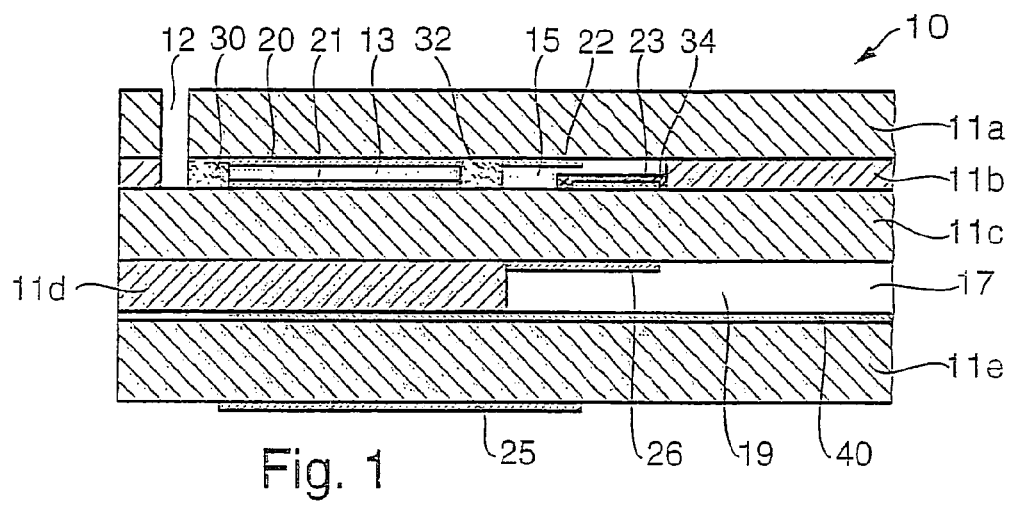
FIG. 1 shows a cross section through a section of a sensor element according to a first exemplary embodiment of the present invention.

FIG. 1 shows a basic design of a first embodiment of the present invention, including a planar sensor element 10 of an electrochemical gas sensor which is used to determine oxygen-containing gases, for example, the nitrogen oxide content of exhaust gases in particular. It has a plurality of oxygen ion-conducting solid electrolyte layers 11a, 11b, 11c, 11d and 11e, which are designed as ceramic films, for example, and form a planar ceramic body. They are made of a solid electrolyte material that conducts oxygen ions, e.g., $ZrO_2$ fully or partially stabilized with $Y_2O_3$.

The integrated form of the planar ceramic body of sensor element 10 is produced by laminating together the ceramic films, which are printed with function layers, and then sintering the laminated structure by a known method.

Sensor element 10 has a first internal gas space 13, which is in contact with the gas mixture to be determined via an orifice 12. Orifice 12 is provided perpendicular to the surface of sensor element 10 in solid electrolyte layer 11a. In addition, a second internal gas space 15 which is preferably connected by a gas-permeable gas diffusion barrier 32 to first internal gas space 13 and a reference gas channel 19 are also provided. Reference gas channel 19 is in contact with a reference gas atmosphere by a gas inlet 17 which leads out of the planar body of sensor element 10 at one end.

A first and a second internal electrodes 20, 21 are situated in first internal gas space 13. There is also another internal electrode 22 in second internal gas space 15. An external electrode 25, which may be covered with a porous protective layer (not shown) is situated on the outer side of solid electrolyte layer 11e directly facing the gas to be analyzed.

Internal electrodes 20, 21, 22 together with external electrode 25 form electrochemical pumping cells. A constant oxygen partial pressure is established by the pumping cells in internal gas spaces 13, 15 of sensor element 10.

At least one internal electrode 20, 21, 22 is additionally connected to a reference electrode 26, which is situated in reference gas channel 19, to form Nernst cells or concentration cells for monitoring the oxygen partial pressure thus established. These concentration cells permit a direct comparison of the oxygen potential of internal electrodes 20, 21, which depends on the oxygen concentration in internal gas spaces 13, 15, with the constant oxygen potential of reference electrode 26 in the form of a measurable electric voltage. The pump voltage applied to the pumping cells is selected to yield a constant voltage across the corresponding concentration cells.

Another internal electrode 23 is provided in internal gas space 15, forming an additional pumping cell together with external electrode 25 or reference gas electrode 26. This pumping cell is used to detect the gas to be determined, the gas to be determined being broken down at the surface of internal electrode 23 and the oxygen thus released being pumped out. The pump current between electrodes 23, 25 and/or 23, 26 is a measure of the concentration of the gas to be determined.

Electrodes 20, 21, 22 are made of a catalytically inactive material to ensure that there is no decomposition of the gas to be determined on electrodes 20, 21, 22. This inactive material may be gold or a gold/platinum alloy, for example. However, electrode 23 is made of a catalytically active material, e.g., rhodium or a platinum/rhodium alloy. External electrode 25 and reference electrode 26 are also made of a catalytically active material such as platinum. The electrode material for all electrodes is used as a cermet in a known manner, so that it will sinter with the ceramic films.

Furthermore, a resistance heater 40 is embedded in the ceramic base body of sensor element 10 between two electric insulation layers (not shown here). Resistance heater 40 is used for heating sensor element 10 to the required operating temperature of 750° C., for example.

A porous diffusion barrier 30 is placed upstream from internal electrodes 20, 21 in the direction of diffusion of the gas mixture within internal gas space 13. Porous diffusion barrier 30 forms a diffusion resistance with respect to the gas diffusing toward internal electrodes 20, 21. Internal gas spaces 13, 15 are separated from one another by additional porous diffusion barrier 32, for example, which makes it possible to establish different oxygen concentrations in internal gas spaces 13, 15.

At least one sintering operation at high temperatures is provided during the production of the sensor element. Since internal electrodes 22, 23 having different material compositions are situated in internal gas space 15, contamination of electrodes 22, 23 with metal constituents of the other type of electrode occurs during the sintering operation. This may result, for example, in partial inactivation of catalytically active electrodes 23 due to gold inclusions, or conversely, an increased catalytic activity of internal electrode 22 due to contamination with rhodium. Both effects significantly impair the sensitive properties of the sensor.

To prevent this phenomenon, according to a first exemplary embodiment of the present invention, a diffusion barrier 34 is placed over one or both electrodes 22, 23. It is made of a porous ceramic material and may additionally contain elementary platinum as a substance which captures metal vapors out of the gas phase. The layer thickness and porosity of diffusion barrier 34 are such that access of the gas to be determined to the surface of electrode 23 is not restricted to any significant extent.

Figure 2:
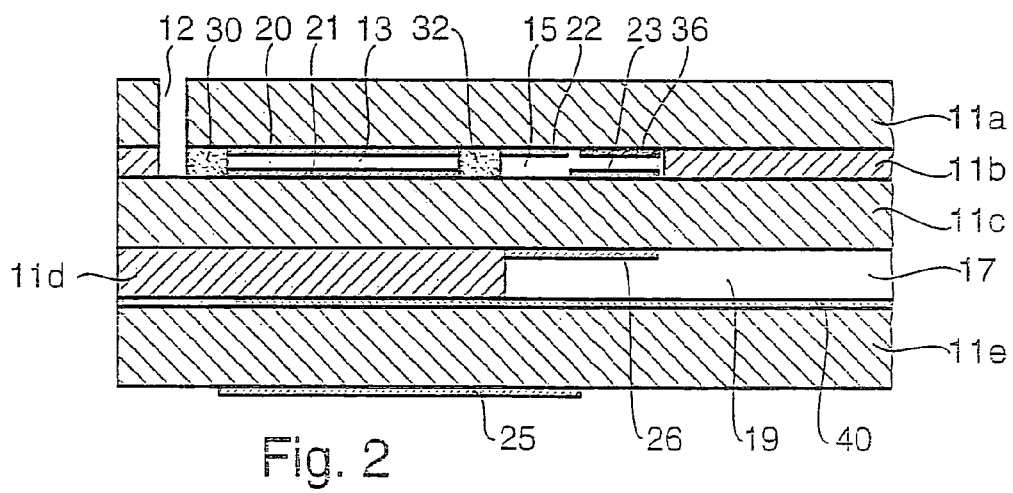
FIG. 2 shows a cross section of a section of a sensor element on the side of the gas to be analyzed according to another exemplary embodiment.

FIG. 2 shows a second exemplary embodiment of the present invention; the reference numbers used in FIG. 2 denote the same components as in FIG. 1.

Figure 3:
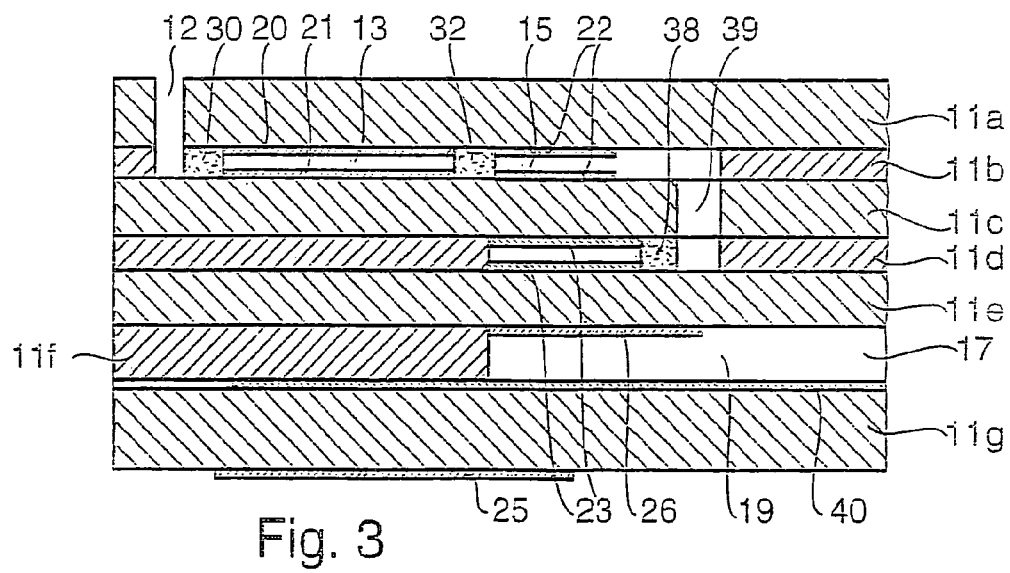
FIG. 3 shows a cross section of a section of a sensor element on the side of the gas to be analyzed according to another exemplary embodiment.

To prevent mutual contamination of electrodes during production, a layer 36 of a material that absorbs metal vapor is applied to the surfaces which border internal gas space 15 in internal gas space 15. Layer 36 may be porous and/or designed as a mesh and contains platinum, for example, as the component that absorbs metal vapor. Layer 36 may also be situated over one electrode 22, 23 with a porous intermediate layer being provided between layer 36 and electrode 22, 23 to prevent direct contact of layer 36 with the surface of electrode 22, 23. Placement of layer 36 on diffusion barrier 32 or on a diffusion barrier 34 according to the first exemplary embodiment is also possible. The effect of platinum as the material which absorbs metal vapor is based mainly on the fact that it is capable of forming stable alloys or at least interstitial compounds with rhodium as well as gold, depending on the concentration range. FIG. 3 shows a third exemplary embodiment of the present invention, the reference numbers used in FIG. 3 denoting the same components as in FIG. 1.

Diffusion path 39 between electrodes 22, 23 is lengthened as a means of preventing mutual contamination of the electrodes, so that diffusion of metal vapor between electrodes 22, 23 is made difficult. It is particularly advantageous for electrode 23 to be situated in a separate layer level 11d of the sensor element, because this results in a definite lengthening of diffusion path 39 between two electrodes 22, 23 without increasing the longitudinal dimension of the sensor element. This arrangement also permits placement of two electrodes 22 and/or 23 within internal gas space 15 as well as the use of an additional diffusion barrier 38 between electrodes 22, 23. Experience has shown that diffusion path 39 is particularly effective when it amounts to at least one or more times the chamber height of internal gas space 15.

Figure 4:
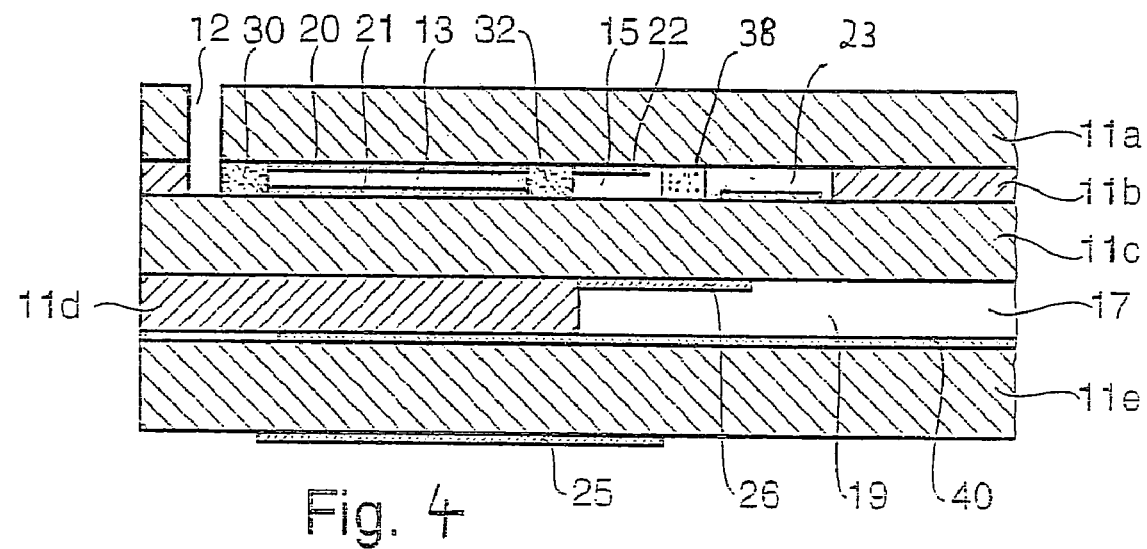
FIG. 4 shows a cross section of a section of a sensor element on the side of the gas to be analyzed according to another exemplary embodiment.

FIG. 4 shows a fourth exemplary embodiment of the present invention, the reference numbers used in FIG. 4 denoting the same components as in FIGS. 1 through 3.

To prevent mutual contamination of electrodes 22, 23, additional diffusion barrier 38 here is provided with a component that absorbs metal vapor, preferably a metallic component such as platinum. The porosity of diffusion barrier 38 is preferably selected so that it does not present any significant diffusion resistance to the gas mixture diffusing toward electrode 23. However, the porosity of the barrier and the concentration of the component that absorbs metal vapor may be varied in the direction of flow of the diffusing gas mixture within diffusion barrier 38.

A combination of the measures on which the third and fourth exemplary embodiments are based with the measures of the first and second exemplary embodiments is also covered by the present invention and would result in a particularly effective means of preventing mutual contamination of the electrodes during the production process.

In addition to the exemplary embodiments of the present invention described here, other embodiments of sensor elements are also conceivable, including electrodes having different material compositions and requiring protection from mutual contamination of the electrodes. This is true, for example, in the case of sensors having mixed potential electrodes for determining gaseous hydrocarbons or hydrogen.

What is claimed is:

1. A sensor element of a gas sensor for determining a concentration of at least one component of a gas mixture, comprising:

at least two electrodes that are situated in an internal gas space that is in direct contact with the gas mixture, a first electrode of the at least two electrodes containing a first material and a second electrode of the at least two electrodes containing a second material; and an arrangement, situated in the internal gas space, for at least one of acting physically and acting chemically to prevent diffusion of metal between the first electrode and the second electrode;

wherein the arrangement includes a first layer containing a material that absorbs metal vapor and is situated on a diffusion barrier separating a first and a second internal gas space;

wherein the diffusion barrier is made of a porous ceramic material that has a component that absorbs metal vapor.

2. The sensor element as recited in claim 1, wherein:

the gas mixture includes an exhaust gas of an internal combustion engine.

3. The sensor element as recited in claim 1, wherein:
the diffusion barrier is situated as a layer on a surface of at least one of the first electrode and the second electrode.

4. The sensor element as recited in claim 1, wherein:
the material that absorbs metal vapor forms at least one of an alloy and an interstitial compound with one of the first material and the second material.

5. The sensor element as recited in claim 4, wherein:
the material that absorbs metal vapor contains platinum.

6. The sensor element as recited in claim 1, wherein:
the first layer is at least one of porous and designed as a mesh.

7. A sensor element of a gas sensor for determining a concentration of at least one component of a gas mixture, comprising:
at least two electrodes that are situated in an internal gas space that is in direct contact with the gas mixture, a first electrode of the at least two electrodes containing a first material and a second electrode of the at least two electrodes containing a second material; and
an arrangement, situated in the internal gas space, for at least one of acting physically and acting chemically to prevent diffusion of metal between the first electrode and the second electrode;
wherein the arrangement includes a first layer containing a material that absorbs metal vapor and is situated on a diffusion barrier separating a first and a second internal gas space; wherein the first layer is situated on a surface of at least one of the first electrode and the second electrode.

8. The sensor element as recited in claim 7, further comprising:
a porous, insulating, intermediate layer formed between the first layer and the surface of at least one of the first electrode and the second electrode.

9. A sensor element of a gas sensor for determining a concentration of at least one component of a gas mixture, comprising:
at least two electrodes that are situated in an internal gas space that is in direct contact with the gas mixture, a first electrode of the at least two electrodes containing a first material and a second electrode of the at least two electrodes containing a second material; and
an arrangement, situated in the internal gas space, for at least one of acting physically and acting chemically to prevent diffusion of metal between the first electrode and the second electrode;
wherein the arrangement includes a first layer containing a material that absorbs metal vapor and is situated on a diffusion barrier separating a first and a second internal gas space; wherein the diffusion barrier and the first layer are integrated.

10. The sensor element as recited in claim 1, wherein:
the first layer is situated in a diffusion path extending between the first electrode and the second electrode.

11. The sensor element as recited in claim 1, wherein:
the arrangement includes a diffusion path between the first electrode and the second electrode, and
a length of the diffusion path corresponds to at least a height of a chamber of the internal gas space.

12. The sensor element as recited in claim 11, wherein:
the diffusion path reaches across at least two layer levels of the sensor element.

* * * * *